US00PP24164P2

(12) United States Plant Patent
Chen

(10) Patent No.: US PP24,164 P2
(45) Date of Patent: Jan. 14, 2014

(54) ***CORDYLINE* PLANT NAMED 'SPRILECSTAR'**

(50) Latin Name: *Cordyline banskii*
Varietal Denomination: Sprilecstar

(75) Inventor: Jianping Chen, Zhejiang (CN)

(73) Assignee: Sprint Horticulture Pty. Ltd., Wamberal, NSW (AU)

( * ) Notice: Subject to any disclaimer, the term of this patent is extended or adjusted under 35 U.S.C. 154(b) by 75 days.

(21) Appl. No.: 13/385,875

(22) Filed: Mar. 10, 2012

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — Annette Para
(74) *Attorney, Agent, or Firm* — C. A. Whealy

(57) ABSTRACT

A new and distinct cultivar of *Cordyline* plant named 'Sprilecstar', characterized by its upright to semi-erect plant habit with foliage initially erect to outwardly arching to close to horizontal; moderately vigorous to vigorous growth habit; freely clumping habit; long lanceolate variegated leaves with dark brown, yellow green and greyed orange to greyed yellow-colored longitudinal stripes; and excellent keeping quality and good garden performance.

3 Drawing Sheets

Botanical designation: *Cordyline banksii.*
Cultivar denomination: 'SPRILECSTAR'.

BACKGROUND OF THE INVENTION

The present invention relates to a new and distinct *Cordyline* plant, botanically known as *Cordyline banksii* and hereinafter referred to by the name 'Sprilecstar'.

The new *Cordyline* plant is a naturally-occurring whole plant mutation of a proprietary selection of *Cordyline banksii* identified as code number CBV50.1, not patented. The new *Cordyline* plant was discovered and selected by the Inventor from within a population of plants of the parent selection in a controlled greenhouse environment in Zhejiang, China in August, 2003.

Asexual reproduction of the new *Cordyline* plant by micropropagated cuttings in Zhejiang, China since 2009 has shown that the unique features of this new *Cordyline* plant are stable and reproduced true to type in successive generations.

SUMMARY OF THE INVENTION

Plants of the new *Cordyline* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sprilecstar'. These characteristics in combination distinguish 'Sprilecstar' as a new and distinct *Cordyline* plant:

1. Upright to semi-erect plant habit with foliage initially erect to outwardly arching to close to horizontal.
2. Moderately vigorous to vigorous growth habit.
3. Freely clumping habit.
4. Long lanceolate variegated leaves with dark brown, yellow green and greyed orange to greyed yellow-colored longitudinal stripes.
5. Excellent keeping quality and good garden performance.

Plants of the new *Cordyline* differ from plants of the parent selection in the following characteristics:

1. Plants of the new *Cordyline* are not as erect as plants of the parent selection.
2. Plants of the new *Cordyline* and the parent selection differ in leaf color as plants of the parent selection have non-variegated purple-colored leaves.

Plants of the new *Cordyline* can be compared to plants of the *Cordyline australis* 'Purple Sensation', not patented. In side-by-side comparisons conducted in Wamberal, New South Wales, Australia, plants of the new *Cordyline* differed primarily from plants of the 'Purple Sensation' in the following characteristics:

1. Plants of the new *Cordyline* were more clumping than plants of 'Purple Sensation'.
2. Leaves of plants of the new *Cordyline* and 'Purple Sensation' differed in color as plants of 'Purple Sensation' had non-variegated purple-colored leaves.

Plants of the new *Cordyline* can also be compared to plants of the *Cordyline banksii* 'Sprilecpink', disclosed in U.S. Plant Pat. No. 19,213. In side-by-side comparisons conducted in Wamberal, New South Wales, Australia, plants of the new *Cordyline* differed primarily from plants of the 'Sprilecpink' in leaf color as leaves of plants of 'Sprilecpink' had red purple, greyed purple and brown-colored longitudinal stripes.

BRIEF DESCRIPTION OF THE PHOTOGRAPHS

The accompanying photographs illustrate the overall appearance of the new *Cordyline* plant showing the colors as true as it is reasonably possible to obtain in colored reproductions of this type. Colors in the photographs may differ slightly from the color values cited in the detailed botanical description which accurately describe the colors of the new *Cordyline* plant.

The photograph on the first sheet comprises side perspective view of a typical plant of 'Sprilecstar' grown in a container.

The photograph on the second sheet is a top perspective view of typical plants of 'Sprilecstar' grown in containers.

The photograph on the third sheet is a close-up view of the base of typical plants of 'Sprilecstar'.

DETAILED BOTANICAL DESCRIPTION

The aforementioned photographs and following observations and measurements describe plants grown during the summer in 17.5-cm containers in a shadehouse in Wamberal, New South Wales, Australia and under conditions and practices which approximate those generally used in commercial *Cordyline* plant production. During the production of the plants, day temperatures ranged from 20° C. to 30° C., night temperatures ranged from 15° C. to 22° C. and light levels ranged from 2,500 to 3,000 foot-candles. Plants were one year old when the photographs and the botanical description were taken. In the following description, color references are made to The Royal Horticultural Society Colour Chart, 2007 Edition, except where general terms of ordinary dictionary significance are used.

Botanical classification: *Cordyline banksii* 'Sprilecstar'.

Parentage: Naturally-occurring whole plant mutation of proprietary selection of *Cordyline banksii* identified as code number CBV50.1, not patented.

Propagation:

*Type*.—By micropropagated cuttings.

*Time to initiate roots, summer*.—About 14 days at temperatures of about 25° C. to 35° C.

*Time to initiate roots, winter*.—About 21 days at temperatures of about 18° C.

*Time to produce a rooted young plant, summer*.—About one to two months at temperatures of about 25° C.

*Time to produce a rooted young plant, winter*.—About two months at temperatures of about 18° C.

*Root description*.—Medium thickness, fleshy; white in color.

*Rooting habit*.—Freely branching; dense.

Plant description:

*Plant and growth habit*.—Upright to semi-erect habit with foliage initially erect to outwardly arching; broadly inverted triangle; non-branching habit; moderately vigorous to vigorous growth habit; moderate to fast growth rate; freely clumping habit typically four to five shoots will develop within five months of planting.

*Plant height*.—About 70 cm.

*Plant diameter or spread*.—About 90 cm.

*Stem diameter*.—About 2.5 cm to 3.4 cm.

Foliage description:

*Orientation*.—Initially erect to outwardly arching to close to horizontal.

*Arrangement*.—Whorled; sessile.

*Length*.—About 55 cm to 63 cm.

*Width*.—About 2.3 cm to 2.9 cm.

*Shape*.—Lanceolate.

*Apex*.—Acute.

*Margin*.—Entire.

*Cross-sectional profile*.—Towards the base, concave, flattening slightly towards the apex.

*Texture, upper and lower surfaces*.—Leathery; corrugated, glabrous.

*Luster, upper and lower surfaces*.—Moderately glossy.

*Venation pattern*.—Parallel.

*Color*.—Developing leaves, upper and lower surfaces: Close to N200B and 199A; towards the apex, close to 146B; margins, close to 146A; towards the base, close to 144D. Fully expanded leaves, upper surface: Primary color, central longitudinal stripes, close to 200A; marginal longitudinal stripes, close to 146A; central longitudinal stripes, towards the apex, close to 165B to 165C and towards the base, 160B, central stripes surrounded by close to 173A; at the base, close to 146A. Fully expanded leaves, lower surface: Primary color, central longitudinal stripes, close to N199A; marginal longitudinal stripes, close to 146A; central longitudinal stripes, close to 173A; at the base, close to 173A with close to 146B towards the margins. Venation, upper and lower surfaces: Similar to surface coloration.

Flower description: Flower initiation and development has not been observed on plants of the new *Cordyline*.

Disease/pest resistance: Plants of the new *Cordyline* have not been shown to be resistant to pathogens and pests common to *Cordyline*.

Keeping quality: Excellent keeping quality; plants of the new *Cordyline* are durable and will maintain good leaf substance indefinitely.

Garden performance: Plants of the new *Cordyline* have been observed to have good garden performance and to tolerate wind, rain and temperatures ranging from about 5° C. to about 45° C.

It is claimed:

1. A new and distinct *Cordyline* plant named 'Sprilecstar' as illustrated and described.

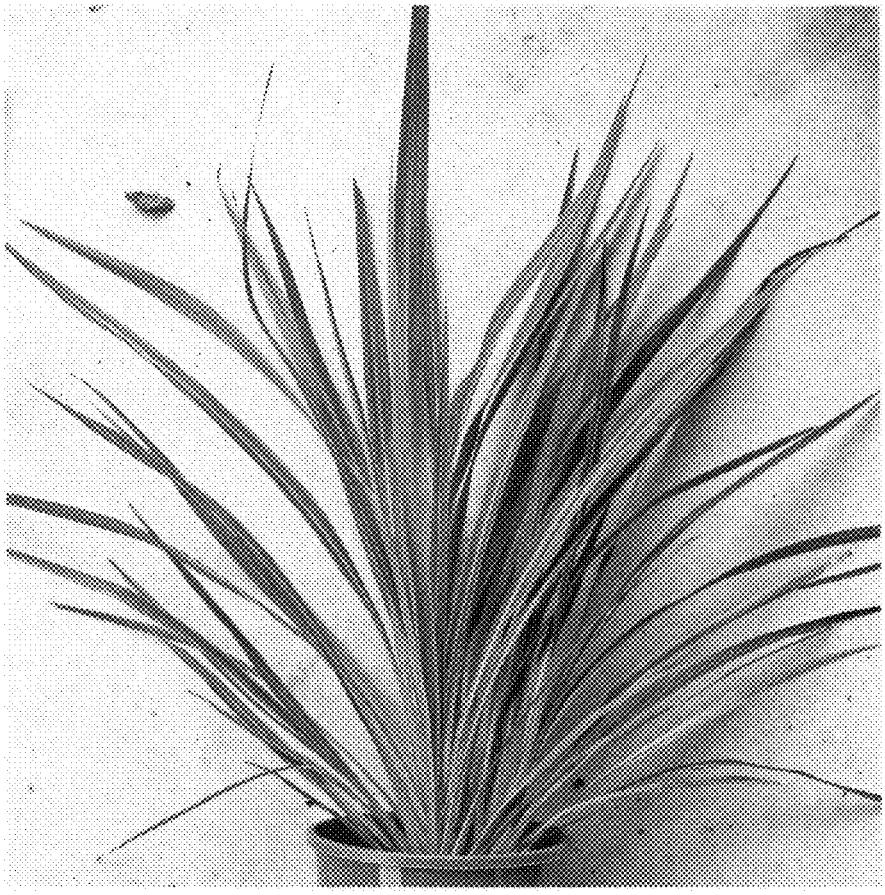

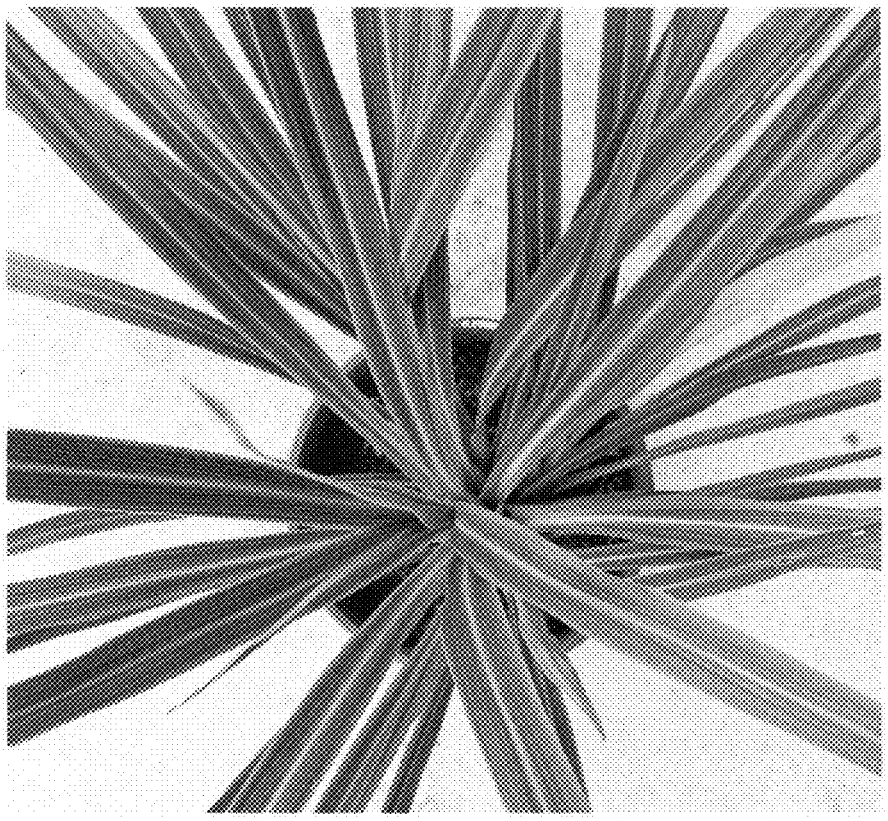

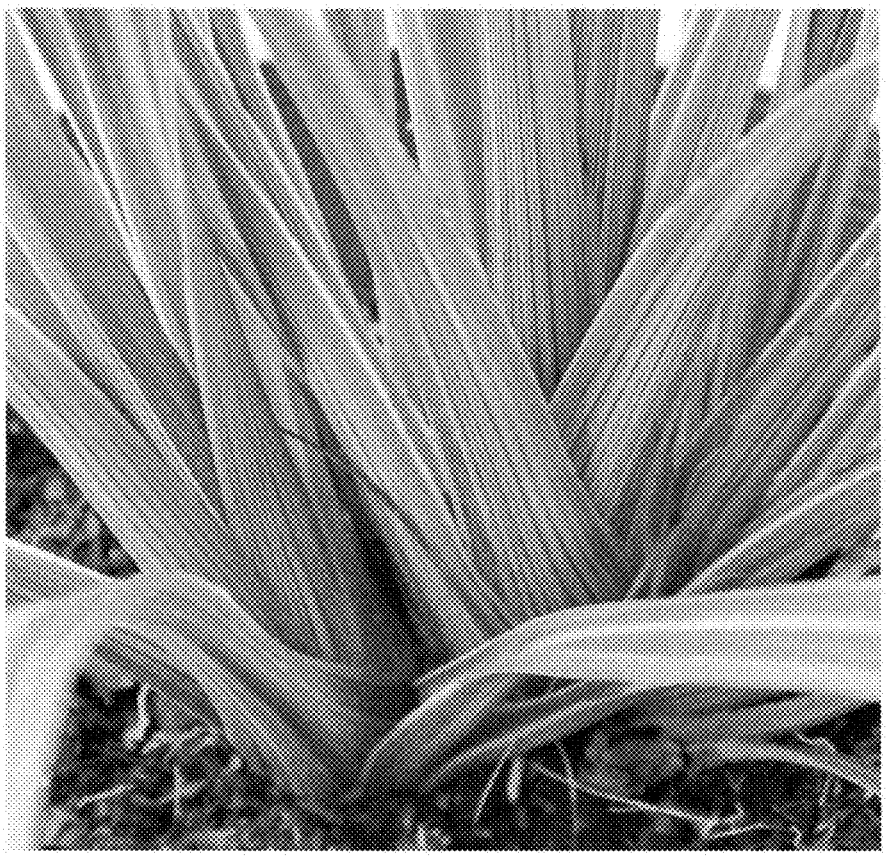

* * * * *